United States Patent [19]
Anthony et al.

[11] Patent Number: 5,298,655
[45] Date of Patent: Mar. 29, 1994

[54] FARNESYL PYROPHOSPHATE ANALOGS

[75] Inventors: Neville J. Anthony, Hatfield; Ta-Jyh Lee; Robert L. Smith, both of Lansdale; Gerald E. Stokker, Gwynedd Valley, all of Pa.

[73] Assignee: Merck & Co., Inc., Rahway, N.J.

[21] Appl. No.: 766,981

[22] Filed: Sep. 27, 1991

[51] Int. Cl.$^5$ .................. C07C 57/02; C07F 9/02; A01N 27/00
[52] U.S. Cl. .................. 562/598; 554/155; 560/183; 562/579; 562/289; 562/555; 562/15; 562/23; 562/24; 558/170
[58] Field of Search ............ 562/579, 589, 598; 560/183; 260/413 L; 514/763; 554/155

[56] References Cited

U.S. PATENT DOCUMENTS

| | | | |
|---|---|---|---|
| 3,173,942 | 3/1965 | Barton et al. | 562/598 |
| 4,259,253 | 3/1981 | Donetti et al. | 554/155 |
| 4,693,849 | 9/1987 | Mignani et al. | 562/598 |
| 4,738,801 | 4/1988 | Tahara et al. | 514/549 |
| 4,837,023 | 6/1989 | Eibl | 424/439 |
| 5,043,268 | 8/1991 | Stock | 435/15 |
| 5,049,552 | 9/1991 | Eibl | 514/77 |

FOREIGN PATENT DOCUMENTS

| | | | |
|---|---|---|---|
| 0108565 | 5/1984 | European Pat. Off. | 562/11 |
| 0356866 | 3/1990 | European Pat. Off. | 526/21 |
| 0442816A1 | 8/1991 | European Pat. Off. | 562/579 |
| 0456180A1 | 11/1991 | European Pat. Off. | C12N 9/10 |
| 3516114A1 | 5/1985 | Fed. Rep. of Germany | 562/579 |
| 1.981M | 5/1962 | France | 562/579 |
| 2209043 | 9/1987 | Japan | 562/598 |
| WO91/16340 | 10/1991 | PCT Int'l Appl. | C07K 7/06 |
| 938712 | 10/1963 | United Kingdom | 562/579 |
| 87/03478 | 6/1987 | World Int. Prop. O. | 562/8 |

OTHER PUBLICATIONS

Goldstein, J. L., et al., "Nonfarnesylated Tetrapeptide Inhibitors of Protein Farnesyltransferase", *The Journal of Biological Chemistry*, vol. 266, No. 24 pp. 15575-15578 (1991).

Pat Abst Jap, Unexamined Appl, C. Field, vol. 12, No. 84, 17-Mar.-88, The Pat Off Jap Government, p. 78 C 482 No. 62-23 (Kuraray Co. Ltd,).

Schaber, et al. Journal Biological Chemistry, vol. 265, No. 25, pp. 14701-14704), Sep. 5, 1990.

Pat Abst Jap, C. Field, vol. 11, No. 369, 2-Dec.-87, Pat Off Jap. Gov., p. 138, C461 No. 62142137. (Kuraray Co. Ltd.).

*Primary Examiner*—JoseACUlel G. Dees
*Assistant Examiner*—Keith MacMillan
*Attorney, Agent, or Firm*—Mark R. Daniel; Joseph F. DiPrima

[57] ABSTRACT

The present invention is directed to farnesyl pyrophosphate analogs which inhibit farnesyl-protein transferase (FTase) and the farnesylation of the oncogene protein Ras. The invention is further directed to chemotherapeutic compositions containing the compounds of this invention, and methods for inhibiting farnesyl-protein transferase and the farnesylation of the oncogene protein Ras.

3 Claims, No Drawings

FARNESYL PYROPHOSPHATE ANALOGS

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbial. Rev.* 53:171-286 (1989). Forms of Ras in cancer cells have mutations that distinguish the protein from Ras in normal cells.

At least three post-translational modifications are involved with Ras membrane localization, and all three modifications occur at the C-terminus of Ras. The Ras C-terminus contains a sequence motif termed a "CAAXII" or "Cys-Aaa$^1$-Aaa$^2$-Xaa" box (Aaa is an aliphatic amino acid, the Xaa is any amino acid) (Willumsen it al., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci.* USA 86:8323 (1989)). In addition, Ha-Ras and N-Ras are palmitoylated via formation of a thioester on a Cys residue near the C-terminal Cys farnesyl acceptor (Gutierrez et al., *EMBO J.* 8:1093-1098 (1989); Hancock et al., *Cell* 57: 1167-1177 (1989)). Ki-Ras lacks the palmitate acceptor Cys. The last three amino acids at the Ras C-terminal end are removed proteolytically, and methyl esterification occurs at the new C-terminus (Hancock it al., ). Fungal mating factor and mammalian nuclear lamins undergo identical modification steps (Anderegg at al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey it al., ; Schafer et al., *Science* 245:379 (1989)). These drugs inhibit HMG-COA reductase, the rate limiting enzyme for the production of polyisoprenoids and the farnesyl pyrophosphate precursor. It has been shown that a farnesyl-protein transferase using farnesyl-pyrophosphate as a requisite cosubstrate is responsible for Ras farnesylation. (Reiss et al., *Cell,* 62: 81-88 (1990); Schaber it al., *J. Bioi. Chem.,* 265:14701-14704 (1990); Schafer et al., *Science,* 249: 1133-1139 (1990); Manne et al., *Proc. Natl. Adad. Sci USA,* 87: 7541-7545 (1990)).

Inhibition of farnesyl-protein transferase and, thereby, farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630-6634(1989)). Cytosol-localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-COA reductase blocks Ras membrane localization in vivo and inhibits Ras function. Inhibition of farnesyl-protein transferase is more specific and is attended by fewer side effects than is the case for a general inhibitor of isoprene biosynthesis.

It is, therefore, an object of this invention to develop farnesyl pyrophosphate analogs which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes farnesyl pyrophosphate analogs which inhibit farnesyl-protein transferase and the farnesylation of the oncogene protein Ras, chemotherapeutic compositions containing the compounds of this invention, and methods for producing the compounds of this invention.

The compounds of this invention are illustrated by the formula:

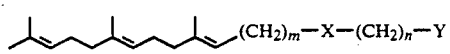

DETAILED DESCRIPTION OF THE INVENTION

The farnesyl pyrophosphate analog compounds of this invention are useful in the inhibition of farnesyl-protein transferase and the farnesylation of the oncogene protein Ras. The compounds of this invention are illustrated by the formula:

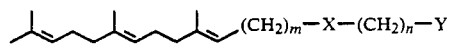

wherein:

X is $CH_2$, $CH(OH)$, $C=O$, $CHCOR$, $CH(NH_2)$, $CH(NHCOR)$, $O$, $S(O)p$, $NH$, $NHCO$,

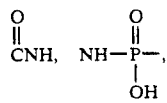

p is 0, 1 or 2;
Y is $PO_3RR^1$ or $CO_2R$;
R is H, lower alkyl, or $CH_2CH_2N^+Me_3A^-$;
$R^1$ is H, lower alkyl, or $CH_2CH_2N^+Me_3A^-$;
$A^-$ is a pharmaceutically acceptable anion;
m is 0, 1, 2 or 3; and
n is 0, 1, 2 or 3;

or the pharmaceutically acceptable salts thereof.

The preferred compounds of this invention include:

| No. of Scheme | Structure | FTase $IC_{50}$ ($\mu M$) |
|---|---|---|
| 1 | (farnesyl)-CH(OH)-$CO_2H$ | 310 |
| 2 | (farnesyl)-C(=O)-$PO_3H_2$ | 62 |
| 3 | (farnesyl)-CH(OH)-$PO_3H_2$ | 100 |
| 4 | (farnesyl)-CH($COCH_3$)-$PO_3H_2$ | 21 |
| 5 | (farnesyl)-$CH_2$-NH-C(=O)-$CH_2$-$PO_3H_2$ | 0.044 |
| 6 | (farnesyl)-S-$CH_2$-$PO_3H_2$ | 100 |
| 7 | (farnesyl)-CH(OH)-$PO_3H_2$ | 0.042 |
| 8 | (farnesyl)-$CH_2$-NH-C(=O)-$CH_2$-$CO_2H$ | 100 |
| 9 | (farnesyl)-CH(OH)-$PO_3H_2$ | 1.7 |
| 10 | (farnesyl)-CH(OH)-$CH_2$-$PO_3H_2$ | 0.42 |
| 11 | (farnesyl)-$CH_2$-NH-C(=O)-$CH_2$-P(=O)(OK)($OCH_3$) | 100 |
| 12 | (farnesyl)-CH(OH)-$PO_3H_2$ | 42 |
| 13 | (farnesyl)-NH-C(=O)-P(=O)(OK)(OK) | 0.22 |
| 14 | (farnesyl)-CH($NHCOCH_3$)-$PO_3H_2$ | 0.18 |

The farnesyl pyrophosphate analog compounds of this invention were tested as follows for their ability to inhibit Ras farnesylation in vitro. Farnesyl-protein transferase from bovine brain was chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3 M NaCl gradient). Ras-CVLS at 3.5 $\mu M$, 0.25 $\mu M$ [$^3H$]FPP, and the indicated compounds were incubated with this partially purified enzyme preparation.

The FTase data presented above are the averages of 2-5 determinations and reflect the ability of the test compounds to inhibit Ras farnesylation in vitro.

In the present invention, lower alkyl, unless otherwise indicated, is 1-7 carbon straight or branched chain saturated alkyl having one or two hydrogens abstracted, and includes methyl, ethyl, propyl, isopropyl, butyl, isobutyl, t-butyl, pentyl, hexyl and heptyl.

The pharmaceutically acceptable salts of the compounds of this invention include the conventional nontoxic salts or the quarternary ammonium salts of the compounds of this invention as formed, e.g., from nontoxic inorganic or organic bases.

The pharmaceutically acceptable salts of the acids of the present invention are readily prepared by conventional procedures such as treating an acidic compound of this invention with an appropriate amount of a base, such as an alkali or alkaline earth metal hydroxide, e.g., sodium, potassium, lithium, calcium or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of this invention inhibit farnesyl-protein transferase and the farnesylation of the oncogene protein Ras. The compounds of this invention are further useful in the inhibition of squalene synthetase. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

The compounds of this invention may be prepared according to the reaction schemes as set forth below.

SCHEME 1

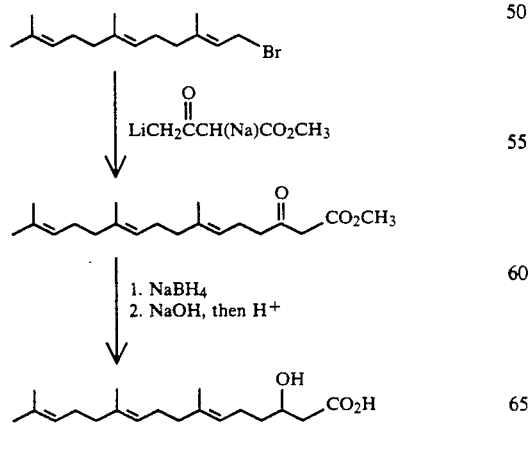

SCHEME 2

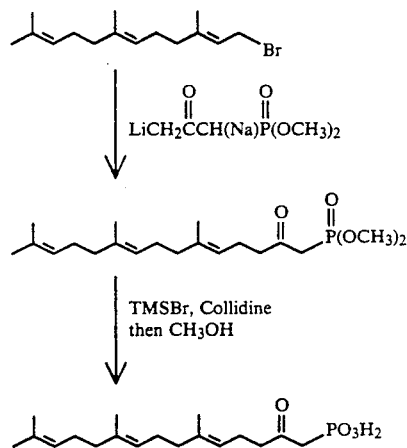

SCHEME 3

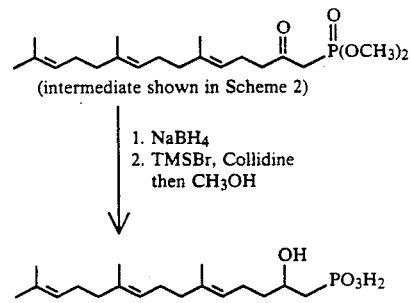

SCHEME 4

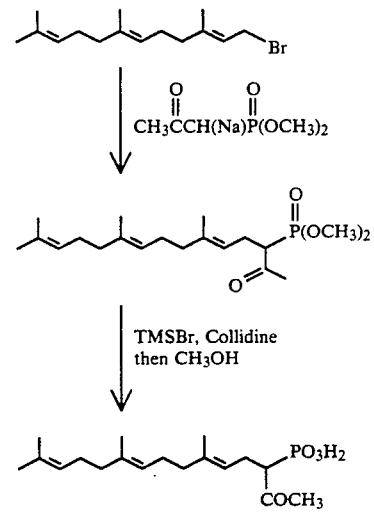

SCHEME 5

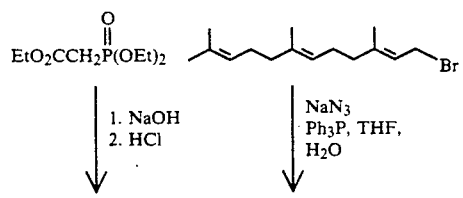

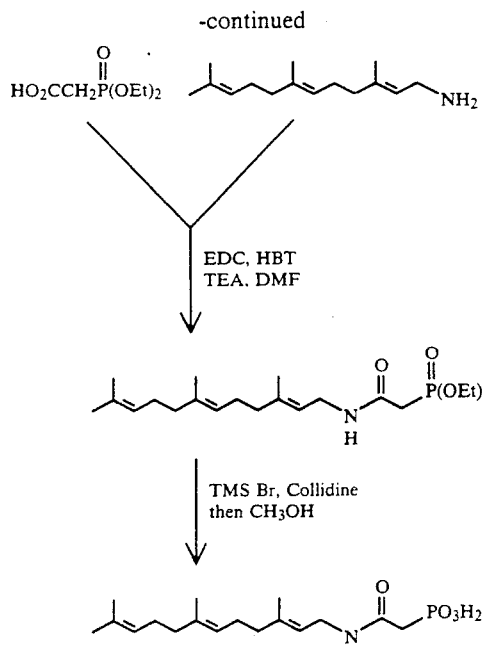
SCHEME 6
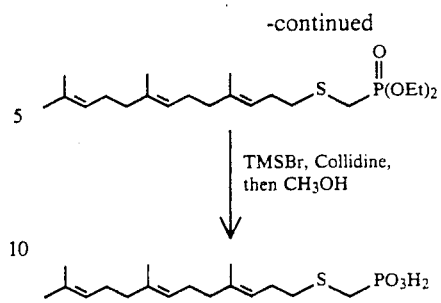
SCHEME 7
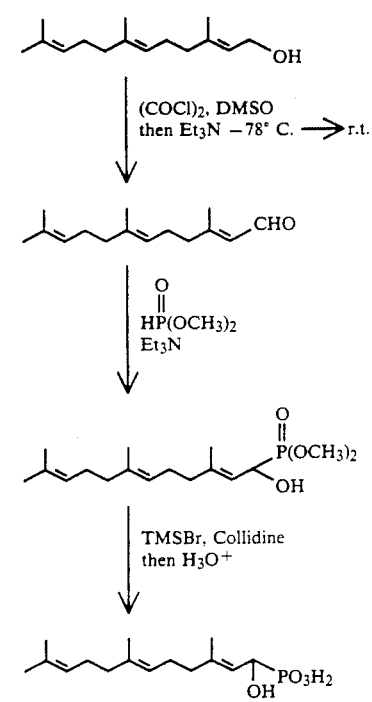
SCHEME 8
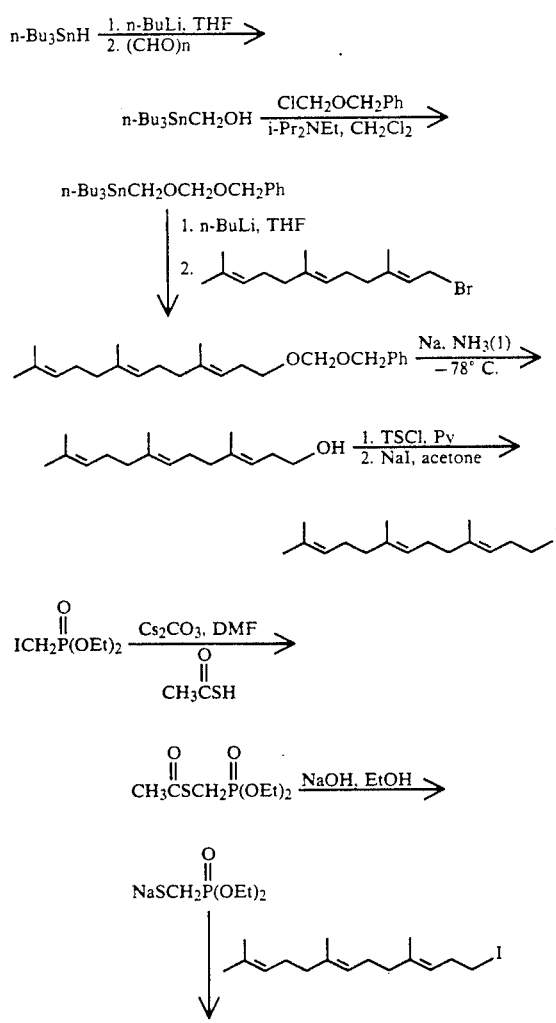
SCHEME 9

5,298,655

-continued

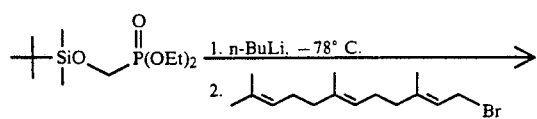
1. n-BuLi, -78° C.
2. [farnesyl bromide]

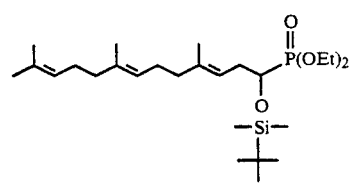

1. n-Bu₄NF, THF
2. TMSBr, Collidine then H₃O⁺

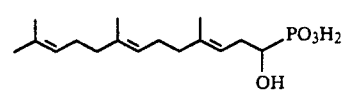

SCHEME 10

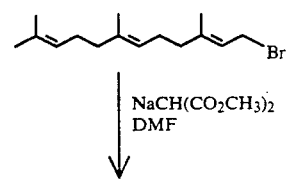

NaCH(CO₂CH₃)₂
DMF

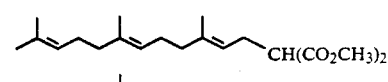

NaCl, DMF,
H₂O, Δ

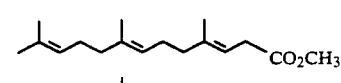

LAH, Et₂O

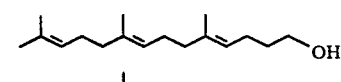

(COCl)₂, DMSO
then Et₃N
-78° → r.t.

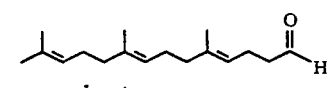

HP(OCH₃)₂ (=O)
NEt₃

-continued

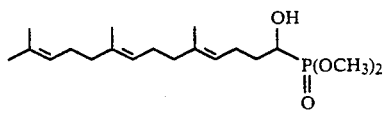

TMSBr, Collidine
then H₃O⁺

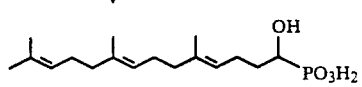

SCHEME 11

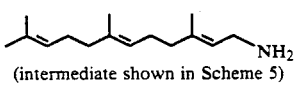
(intermediate shown in Scheme 5)

HO₂CCH₂P(OCH₃)₂ (=O)
EDC, HBT
TEA, DMF

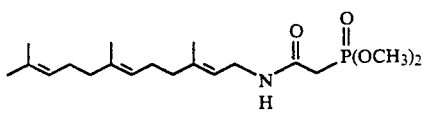

KOH, CH₃OH
H₂O, Δ

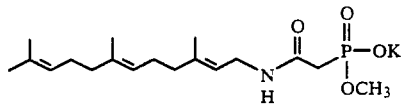

SCHEME 12

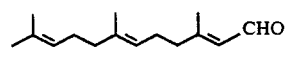
(intermediate shown in Scheme 7)

LiCH₂P(OCH₃)₂ (=O)

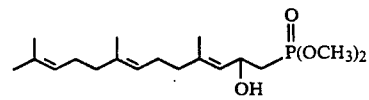

TMSBr, Collidine
then H₃O⁺

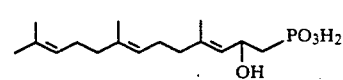

SCHEME 13

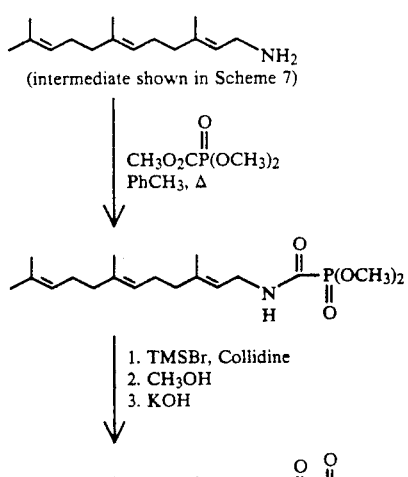

(intermediate shown in Scheme 7)

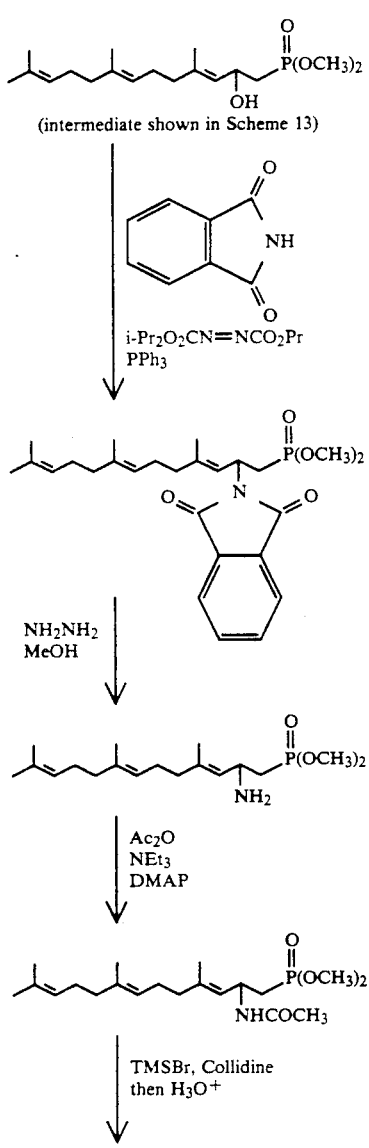

SCHEME 14

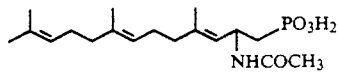

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of 3-Hydroxy-7,11,15-trimethylhexadeca-6.10.14-trienoic acid

Step 1: Methyl 3-oxo-7,11,15-trimethylhexadeca-6,10,14-trienoate

Methyl acetoacetate (225 μL, 2.1 mmol) was added dropwise to a stirred suspension of sodium hydride (50% oil suspension, prewashed with hexane) (100 mg, 2.1 mmol) in anhydrous THF (5 mL) at 0° C. under an Argon atmosphere. The resulting solution was stirred 15 minutes at 0° C. and then treated with a 1.6 M solution (1.3 mL, 2.1 mmol) of n-butyllithium in hexane over 2 minutes. The yellow solution was stirred 15 min at 0° C. and then treated dropwise with farnesyl bromide (545 KL, 2.0 mmol). The cloudy orange solution was stirred at 20° C. for 1 ½ hours and then quenched by dropwise addition of saturated aqueous NH$_4$Cl solution. The resulting mixture was diluted with ethyl acetate and washed with water, dried, filtered and evaporated to give the crude product which was used in the next step without purification. Diagnostic peaks in the NMR (300 MHz, CDCl$_3$): δ 1.600 (6H, s), 1.614 (3H,s), 1.68 (3H, s), 1.9–2.1 (8H, m), 2.2–2.33 (2H, m), 2.58 (2H, t, J=6Hz), 3.448 (2H, s), 3.740 (3H,s), 5.05–5.15 (3H, m).

Step 2: Methyl 3-hydroxy-7,11,15-trimethylhexadeca-6,10,14-trienoate

Powdered sodium borohydride (38 mg, 1.0 mmol) was added at 0° C. to a stirred solution of methyl 3-oxo-7,11,15-trimethylhexadeca-6,10,14-trienoate (580 mg, 1.8 mmol) in methanol (5 mL) in one portion. The resulting mixture was stirred at 0° C. for 15 minutes, then treated with a saturated aqueous solution of NH$_4$Cl (2 mL). The resulting mixture was extracted with diethyl ether. This extract was washed with water, dried, filtered and evaporated to give the crude product which was purified by flash chromatography. Elution of the column with hexane:ethyl acetate (10:1/v:v) afforded the title compound as a colorless gum.

H$^1$NMR (300 MHz, CDCl$_3$): δ1.600 (6H, s), 1.622 (3H,s), 1.681 (3H, s), 1.9–2.2 (12H, m), 2.38–2.55 (2H, m), 3.717 (3H, s) 3.95–4.05 (H, m), 5.05–5.15 (3H, m).

Step 3: 3-Hydroxy-7,11,15-trimethylhexadeca-6,10,14-trienoic acid

A solution of methyl 3-hydroxy-7,11,15-trimethyl-hexadeca-6,10,14-trienoate (139 mg, 430 μmol), ethanol (1 mL) and sodium hydroxide (1N, 440 μL, 440 μmol) was stirred at room temperature for two hours. The crude mixture was purified by flash chromatography on a 20 mm ID silica gel column. Elution of the column with choloform:acetic acid (40:1/v=v) gave title compound as a colorless gum.

Anal for $C_{19}H_{32}O_3.0.25\ H_2O$: Calc'd C, 72.91; H, 10.49; Found: C, 73.20; H, 10.39.

$H^1$NMR (300 MHz, $CDCl_3$): $\delta$1.599 (6H, S), 1.629 (3H,s), 1.682 (3H, s), 1.9–2.2 (12H, m), 2.45–2.65 (2H, m), 4.0–4.1 (H, m), 5.05–5.20 (3H, m).

EXAMPLE 2

Preparation of [2-Oxo-6,10,14-trimethylpentadeca-5,9,13-trienyl]phosphonic acid

Step 1: Dimethyl [2-Oxo-6,10,14-trimethylpentadeca-5,9,13-trienyl]-phosphonate This compound was prepared exactly by the method described in Step 1 of Example 1 except that the methyl acetoacetate was replaced by dimethyl 2-oxopropylphosphonate. Thereby was obtained title compound after chromatography on a 30 mm ID silica gel column. Elution of the column with hexane:ethyl acetate:methanol (40:10:2/v:v:v) gave the pure title compound as a colorless gum.

$H^1$ NMR (300 MHz, $CDCl_3$): $\delta$1.56–1.68 (12H,m), 1.92–2.1 (8H, m), 2.25 (h, d, J=6Hz), 2.3 (H, d, J=6Hz), 2.64 (2H, t, J=6Hz), 3.08 (2H, d, J=24Hz), 3.785 (6H, d, J=12Hz), 5.06–5.16 (3H, m).

Step 2: [2-oxo-6,10,14-trimethylpentadeca-5,9,13-trienyl]phosphonic acid 2,4,6-Collidine (225 μL, 1.7 mmol) was added to a stirred solution of dimethyl (2-oxo-6,10,14-trimethylpendadeca-5,9,13-trienyl]phosphonate (315 mg, 850 pmol) in chloroform (5 mL) at 0° C. under Ar atmosphere and this was followed by trimethylsilyl bromide (450 μL, 3.4 mmol). The cooling bath was removed and the clear solution was stirred at ambient temperature for 18 hours. The reaction mixture was evaporated, toluene (3 mL) was added and the mixture was again evaporated to remove any traces of trimethylsilyl bromide or HBr. Distributed white residue between 0.1 N HCl (10 mL) and ethyl acetate (40 mL) at 0° C. The organic layer was separated, washed with cold water (3×10 mL), dried, filtered and evaporated. The crude product was purified by flash chromatography on a 20 mm ID Dowex 50 w-x-y column. Elution of the column with 25% aqueous methanol gave title compound after lyophilization of the appropriate fractions as a light brown gum.

Anal. for $C_{18}H_{31}O_4P.H_2O$: Calc'd: C, 59.98; H, 9.32; Found: C, 60.34; H, 9.21.

$H^1$NMR (300 MHz, $CD_3OD$): $\delta$1.60 (6H,s), 1.63 (3H, s), 1.67 (3H, s), 1.94–2.12 (8H, m), 2.24 (H, d, J=6Hz), 2.28 (H, d, J=6Hz), 2.68 (2H, t, J=6Hz), 3.06 (2H, d, J=24Hz), 5.05–5.15 (3H, m).

EXAMPLE 3

Preparation of [2-Hydroxy-6,10,14-trimethylpentadeca-5,9,13-trienyl]-phosphonic acid This compound was prepared similarly by the method described in Step 2 of Example 1 except that methyl 3-oxo-7,11,15-trimethylhexadeca-6,10,14-trienoate was replaced by dimethyl [2-oxo-6,10, 14-trimethylpentadeca-5,9,13-trienyl]phosphonate and the product from this reaction was used in the hydrolysis step similarly to the method used in Step 2 in Example 2 to give, after lyophilization, title compound as a nearly colorless gum.

Anal. for $C_{18}H_{33}O_4P.0.5\ H_2O$: Calc'd: C, 61.17; H, 9.69; Found: C, 61.22; H, 9.67.

$H^1$NMR (300 MHz, $CD_3OD$): $\delta$1.60 (6H,s), 1.63 (3H, s), 1.67 (3H, s), 1.86–2.2 (14H, m), 3.9–4.0 (H, m), 5.05–5.2 (3H, m).

EXAMPLE 4

Preparation of [1-Acetyl-4,8,12-trimethyltrideca-3,7,11-trienyl]phosphonic acid

Step 1: Dimethyl [1-acetyl-4,8,12-trimethyltrideca-3,7,11-trienyl]phosphonate Dimethyl 2-oxopropylphosphonate (560 μL, 4.0 mmol) was added dropwise to a stirred suspension of sodium hydride (50% oil suspension, prewashed with hexane) (210 mg, 4.8 mmol) in anhydrous THF (15 mL) at 20° C. under an Argon atmosphere. The resulting slurry was stirred at 20° C. for 2 hours to allow for complete formation of the sodio derivative and then treated dropwise with farnesyl bromide (1.14 mL, 4.2 mmol). The cloudy yellow mixture was stirred at 20° C. for 2 hours and then quenched with saturated $NH_4Cl$ solution. The resulting mixture was washed with water, dried, filtered and evaporated to give the crude product which was purified by flash chromatography on a silica gel column. Elution of the column with hexane:ethyl acetate:methanol (40:10:1, v:v:v) gave the title compound as gum.

$H^1$ NMR (300 MHz, $CDCl_3$): $\delta$1.53–1.7 (12H, m), 1.93–2.1 (8H, m), 2.28 (3H, s) 2.4–2.55 (H, m), 2.63–2.8 (H, m), 3.13–3.6 (H, m), 3.78 (6H, d, J=9Hz), 4.95–5.13 (3H, m).

Step 2: [1-Acetyl-4,8,12-trimethyltrideca-3,7,11-trienyl]phosphonic acid

This compound was prepared exactly by the method described in Step 2 of Example 2 except that dimethyl [2-oxo-6,10,14-trimethylpentadeca-5,9,13-trienyl]phosphonate was replaced by dimethyl [1-acetyl-4,8,12-trimethyltrideca-3,7,11-trienyl]phosphonate. Thereby was obtained title compound as a colorless gum.

Anal. for $C_{18}H_{31}O_4P.0.65\ CH_3OH$: Calc'd: C, 61.66; H, 9.32; Found: C, 61.66; H, 9.34.

$H^1$NMR (300 MHz, $CD_3OD$): $\delta$1.59 (6H,s), 1.65 (3H, s), 1.67 (3H, s), 1.9–2.12 (8H, M), 2.25 (3H, S), 2.36–2.50 (H, m), 2.62–2.82 (H, m), 3.1–3.27 (H,m), 5.0–5.17 (3H, m).

EXAMPLE 5

Preparation of [2-[(E,E)-3,7,11-Trimethyl-2,6,10-dodecatrienylamino]-2-oxo-ethyl]phosphonic acid

Step 1: (E,E)-3,7,11-Trimethyl-2,6,10-dodecatrienyl-azide

A mixture of (E,E)-3,7,11-trimethyl-2,6,10-dodecatrienyl bromide (1.5 g, 5.26 mmol) and sodium azide (0.68 g, 10.5 mmol) in DMF (20 mL) was stirred at room temperature for 0.5 hours, then poured into cold water and extracted with ether. The ethereal extract was washed with brine, dried, filtered and evaporated to yield a residue. Purification of the residue by flash chromatography on a silica gel column, using hexane as the eluant, afforded the title compound as an oil (1.2 g, 4.85 mmol, 92%) NMR (CDCl$_3$): δ5.35 (H, t, J=7Hz), 5.10 (2H, m), 3.78 (2H, d, J=7Hz), 1.9–2.2 (8H, m), 1.72 (3H, s), 1.68 (3H, s) 1.60 (6H, s).

Step 2: Diethyl Carboxymethylphonate

Sodium hydroxide (0.54 g, 13.4 mmol) in water (2 mL) was added to a stirred solution of triethyl phosphonoacetate (2 g, 8.9 mmol) in ethanol (10 mL). The resulting mixture was stirred for 1 hour, then acidified with concentrated hydrochloric acid (12N, ca. 40 drops by transfer pipette). The solvents were evaporated under vacuum and the residue was treated with methylene chloride and anhydrous MgSO$_4$. The inorganic salts were filtered off and the filtrate was concentrated in vacuo to give the title compound as an oil (1.7 g, 8.7 mmol, 98%).

NMR (CDCl$_3$): δ8.87 (H, bs), 4.2 (4H, m), 3.06 (2H, s), 1.34 (6H, t, J=7Hz).

Step 3: (E,E)-3,7,11-trimethyl-2,6,10-dodecatrienylamine

Water (46 μL) was added to a stirred mixture of (E,E)-3,7,11-trimethyl-2,6,10-dodecatrienylazide (0.8 g, 3.2 mmol) and triphenylphosphine (0.94 g, 3.62 mmol) in THF (3 mL) and stirred at room temperature overnight. An additional amount of water (46 ML) was added and stirred for another two hours. The reaction mixture was evaporated to dryness and the residue was redissolved in methylene chloride, then MgSO$_4$ was added and filtered. The filtrate was concentrated in vacuo to give the crude title compound as an oily solid which was used in the next step without purification.

Step 4: Diethyl [2-[(E,E)-3,7,11-trimethyl-2,6,10-dodecatrienyl-amino]-2-oxo-ethyl]phosphonate To a stirred solution of the crude (E,E)-3,7,11-trimethyl-2,6,10-dodecatrienyl-amine prepared from the previous reaction and diethyl carboxymethylphonate (0.63 g, 3.2 mmol) and DMF (6 mL) was added 1-hydroxybenzotriazole (0.49 g, 3.2 mmol) and 1-ethyl-3-(3-dimethylaminopropyl)-carbodimide hydrochloride (0.61 g, 3.2 mmol). The resulting mixture was treated with triethylamine to adjust its pH value to 8-8.5, then stirred at room temperature overnight. The reaction mixture was poured into 10% citric acid solution and extracted with ethyl acetate. The organic extract was washed with sodium bicarbonate solution and brine, dried and filtered. Evaporation of the filtrate gave a residue which was purified by flash chromatography on a silica gel column. Elution of the column with 15% acetone in methylene chloride provided the title compound (0.325 g, 0.81 mmol, 25% over two steps) as a viscous oil.

NMR (CDCl$_3$): δ6.64 (H, bs), 5.20 (H, t, J=7Hz), 5.08 (2H, t, J=7Hz), 4.15 (4H, m), 3.87 (2H, t, J=7Hz), 2.88 (H, s), 2.80 (H, s), 2.0 (8H, m), 1.68 (3H, s), 1.60 (3H, s), 1.34 (6H, t, J=7Hz).

Step 5: [2-[(E,E)-3,7,11-Trimethyl-2,6,10-dodecatrienylaminol-2-oxo-ethyl]phosphonic acid Diethyl [2-[(E,E)-3,7,11-trimethyl-2,6,10-dodecatrienylamino]-2-oxo-ethyl]phosphonate (0.325 g, 0.81 mmol) was deprotected in a similar fashion as that described in Step 2 of Example 2. The reaction mixture was diluted with toluene, then evaporated. This process was repeated two more times. The final residue was treated with diluted hydrochloride acid (0.1N) and extracted with ethyl acetate. The extract was washed with water three times, then dried and filtered. Evaporation of the filtrate afforded the title compound (0.14 g, 0.38 mmol, 47%) as an amorphous powder.

Anal for C$_{17}$H$_{32}$NO$_5$P.H$_2$O: Calc: C, 56.49; H, 8.93; N, 3.88; Found: C, 56.46; H, 8.30; N, 4.10.

NMR (CD$_3$OD): δδ 5.13 (H, t, J=7Hz), 5.0 (2H, m), 3.70 (2H, d, J=7Hz), 2.72 (H, s), 2.65 (H, s), 1.8–2.1 (8H, m), 1.60 (3H, s), 1.57 (3H, s), 1.48 (6H,s).

EXAMPLE 6

Preparation of ((E,E)-4,8,12-trimethyl-3,7,11-tridecatrienyl]thiomethyl-phosphonic acid

Step 1: (Benzyloxymethoxy)methyl-tri-(n-butyl)tin n-Butyl lithium (1.6 M in hexane, 16 mL, 25 mmol) was added under nitrogen to a stirred solution of di-isopropylamine (2.88, 28 mmol) in THF (50 mL) at 0° C. The resulting mixture was stirred at 0° C. for 15 min. then added tri-(n-butyl)tin(6.5 ml, 25 mmol) and stirred at 0° C. for 0.5 hours followed by the addition of paraformaldehyde (0.8 g, 25 mmol). The resulting mixture was stirred at 0° C. for 5 minutes, then warmed to room temperature and stirring continued for 1.5 hours. The reaction mixture was poured into cold water and extracted with ether. The ethereal extract was dried, filtered and evaporated to yield a residue (ca. 7.4 g) which was redissolved in methylene chloride (45 mL) and treated with di-isopropylethylamine (9 mL) and benzyl chloromethyl ether (6 mL). The resulting mixture was stirred at room temperature overnight. The reaction mixture was poured into ice chilled diluted hydrochloric acid and extracted with ether. The extract was washed with water, dried, filtered and evaporated to afford an oily residue, which was purified by flash chromatography on a silica gel column. Elution of the column with hexane:ether (50:1, v:v) provided the title compound (8.6 g, 19.5 mmol, 78%) as a colorless oil.

NMR (CDCl$_3$) δ7.25–7.4 (5H, m), 4.66 (2H, s), 4.56 (2H, s), 3.82 (2H, t, J=8Hz), 1.55 (6H, m), 1.3 (6H, m), 0.9 (15H, m).

Step 2: Benzyl [(E,E)-4,8,12-trimethyl-3,7,11-tridecatrienyoxy]methyl ether n-Butyl lithium (1.6M in hexane, 8.6 mL, 13.8 mmol) was added under nitrogen to a stirred solution of (benzyloxymethoxy)methyl-tri-(n-butyl) tin (6.1 g, 13.8 mmol) in THF (56 mL) at −78° C. The resulting mixture was stirred at −78° C. for 10 min, then added a solution of (E,E)-3,7,11-trimethyl-2,6,10-dodecatrienyl-bromide (3.5 g, 12.3 mmol) in THF (4 mL) via a dropping funnel. The resulting mixture was stirred at −78° C. for 0.5 hours, then poured into cold water and extracted with ether. The ethereal extract was dried, filtered and evaporated to afford a residue, which was purified by flash chromatography on a silica gel column. Elution of the column with hexane:ether (25:1, v:v) provided the title compound as a colorless oil (2.39 g, 6.7 mmol, 54.5%).

NMR (CDCl$_3$) δ7.25–7.4 (5H, 5.17 (H, t, J=7Hz), 5.10 (2H, m), 4.78 (2H, s), 4.62 (2H, s), 3.60 (2H, t, J=7 Hz), 2.33 (2H, q, J=7 Hz), 2.0 (8H, m), 1.67 (3H, s), 1.63 (3H, s), 1.59 (6H, s).

Step 3: (E,E)-4,8,12-trimethyl-3,7,11-tridecatrienol

Benzyl [(E,E)-4,8,12-trimethyl-3,7,11-trienyloxy]methyl ether (2.50 g, 7.0 mmol) was added to a 3-necked Bantam-ware, equipped with a mechanical stirrer and filled with ca.60 mL of liquid ammonia. The resulting mixture was stirred at $-78°$ C. while spheres of sodium (total weight ca 1.2 g) was added during a period of 1.5 hours. At this point, TLC analysis of an aliquot indicated the incompletion of the reaction. Therefore, THF (25 ML) was added to increase the fluidity of the reaction mixture followed by the treatment of an additional amount of sodium (ca 0.7 g). Then, it gave a persistent blue color of the reaction mixture. The cooling bath was removed and the reaction mixture was allowed to warm to room temperature. Ammonia was evaporated during the overnight standing. Ethanol (20 mL) was added to the reaction flask, stirred for 10 min, then added water (10 mL) and ether (50 mL). After 5 minute stirring, the mixture was poured into cold water and extracted with ether. The organic layer was separated, dried and filtered. Evaporation of the filtrate gave the title compound (1.66 g, 7.0 mmol, 100%) as a colorless oil.

NMR (CDCl$_3$) $\delta$5.15-5.20 (3H, m), 3.62 (2H, t, J=7Hz), 2.30 (2H, q, J=7Hz), 1.9-2.2 (8H, m), 1.69 (3H, s), 1.65 (3H, s), 1.60 (6H, s).

Step 4: (E,E)-4,8,12-trimethyl-3,7,11-tridecatrienyl tosylate

Tosylchloride (3.51 g, 9 mmol) was added to a stirred solution of (E,E)-4,8,12-trimethyl-3,7,11-tridecatrienol (1.66 g, 7 mmol) in pyridine (30 mL) at 0° C. The resulting mixture was placed in a refrigerator overnight, then poured into cold water and extracted with ether. The ethereal extract was washed with diluted hydrochloric acid to remove pyridine. After drying and filtration, the filtrate was evaporated to afford the title compound as an oil which was used in the next step without purification.

NMR (CDCl$_3$) $\delta$7.79 (2H, d, J=7Hz), 7.33 (2H, d, J=7Hz), 5.07 (2H, q, J=7Hz), 4.96 (H, t, J=7Hz), 3.97 (2H, t, J=7Hz), 2.44 (3H, a), 2.35 (2H, q, J=7Hz), 1.9-2.1 (8H, m), 1.69 (3H, s), 1.60 (3H, s), 1.58 (3H, s), 1.56 (3H, s).

Step 5: (E,E)-4,8,12-trimethyl-3,7,11-tridecatrienyl iodide

The (E,E)-4,8,12-trimethyl-3,7,11-tridecatrienyl tosylate obtained from previous step was dissolved in acetone (50 mL), then added sodium iodide (3.30 g, 22 mmol) and the resulting mixture was stirred at room temperature for 0.5 hours followed by heating at reflux for 3 hours. After cooling, the reaction mixture was poured into cold aqueous sodium thiosulfate solution and extracted with ether. The ethereal extract was washed with water, dried and filtered. Evaporation of the filtrate left a residue which was purified by flash chromatography on a silica gel column. Elution of the column with Hexane:ether (50:1, v:v) provided the title compound (1.85 g, 5.34 mmol, 76% for two steps) as a colorless oil.

NMR (CDCl$_3$) $\delta$8 5.1 (3H, m), 3.12 (2H, t, J=7Hz), 2.60 (2H, q, J=7Hz), 1.95-2.15 (8H, m), 1.69 (3H, s), 1.61 (3H, s), 1.60 (6H, S).

Step 6: Diethyl Acetylthiomethylphosphonanate

To s stirred solution of diethyl idomethylphophonate (1.0 g, 3.6 mmol) in DMF (10 mL) was successively added cesium carbonate (1.30 g, 4 mmol) and thiolacetic acid (0.285 ml, 0.304 g, 4 mmol). The resulting mixture was stirred at room temperature under nitrogen overnight. The reaction mixture was poured into cold water (60 mL) and extracted with ether. The ethereal extract was washed with water (40 mL), dried, filtered and evaporated to yield an oily residue. The original aqueous phase and the washing were then combined and extracted with methylene chloride twice (2×50 mL) and ether once (50 mL). These extracts were combined, dried and filtered. The filtrate was concentrated on a rotary evaporator, then under high vacuum to give an oily residue. The two residue were combined and purified by flash chromatography on a silica gel column. Elution of the column with methylene chloride:acetone (10:1, v:v) afforded the title compound (0.726 g, 3.21 mmol, 89%) as a colorless oil.

NMR (CDCl$_3$) $\delta$4.16 (4H, m), 3.27 (H, s), 3.20 (H, s), 2.40 (3H, s), 1.33 (6H, t, J=7Hz)

Step 7: Diethyl [(E,E)-4,8,12-trimethyl-3,7,11-tridecatrienyl]thiomethylphosphonate Solid sodium hydroxide (0.14 g, 3.5 mmol) was added to a stirred solution of diethyl acetylthiomethylphosphonate (0.59 g, 2.5 mmol) in ethanol (10 mL). The resulting mixture was stirred at room temperature under nitrogen until all the sodium hydroxide dissolved, then added a solution of (E,E)-4,8,12-trimethyl-3,7,11-tridecatrienyl iodide (0.84 g, 2.4 mmol) in ethanol (2 mL). The resulting mixture was stirred at room temperature under nitrogen overnight. The reaction mixture was poured into cold water and extracted with ether. The ethereal extract was washed with water, dried, filtered and evaporated to give a residue, which was purified by flash chromatography on a silica gel column. Elution of the column with methylene:acetate (10:1, v:v) afforded the title compound (0.91 g, 2.26 mmol, 94%) as a colorless oil.

NMR (CDCl$_3$) $\delta$5.17 (H, t, J=7Hz), 5.10 (2H, m), 4.17 (4H, m), 2.65-2.80 (4H, m), 2.30 (2H, q, J=7Hz), 1.9-2.1 (8H, m), 1.68 (3H, s), 1.62 (3H, s), 1.60 (6H, s), 1.35 (6H, t, J=7Hz).

Step 8: [(E,E)-4,8,12-trimethyl-3,7,11-tridecatrienyl]thiomethylphosphonic acid Diethyl [(E,E)-4,8,12-trimethyl-3,7,11-tridecatrienyl9 thiomethylphosphonate (0.256 g, 0.636 mmol) was deprotected in a similar fashion as that described in Step 2 of Example 2. The reaction mixture was added toluene (3 mL), then evaporated in vacuo. This process was repeated two more times. The final residue was treated with diluted hydrochloride acid (0.1N) at 0° C., then extracted with ethylacetate. The extract was washed with water the three time (3×10 ML). After drying and filtration, filtrate was concentrated in vacuo to give the title compound (0.1 g, 0.29 mmol, 45%) as a gum.

Anal for $C_{17}H_{31}O_3PS.0.6\ H_220$ Calcd C 57.15; H, 9.09; Found C, 57.00; H, 9.27.

NMR (CDCl$_3$) $\delta$5.1-5.2 (3H, m), 3.6-3.8 (4H, m), 2.29 (2H, q, J=7Hz), 1.9-2.1 (8H, m), 1.68 (3H, s), 1.63 (3H, s), 1.61 (6H, s).

EXAMPLE 7

Preparation of 3-[(E,E)-3,7,11-trimethyl-2,6,10-dodecatrienylamino]-3-oxo-propionic acid

Step 1: Ethyl 3-[(E,E)-3,7,11-trimethyl-2,6,10-dodecatrienylamino]-3-oxo-propionate The reaction was performed in a similar manner as that described in Step 4 of Example 4 but using malonic acid monoethyl ester instead of diethyl carboxymethylphosphonate. The title compound was obtained as a colorless oil.

NMR (CDCl$_3$) δ7.00 (H, bs), 5.23 (H, t, J=7Hz), 5.12 (2H, m), 4.20 (2H, q, J=7Hz), 3.90 (2H, t, j=7Hz), 3.32 (2H, s), 1.9–2.1 (8H, m), 1.70 (6H, s), 1.61 (6H, s).

Step 2: 3-[(E,E)-3,7,11-trimethyl-2,6,10-dodecatrienylamino]-3-oxo-propionic acid Sodium hydroxide (1 N, 0.68 mL, 0.68 mmol) was added to a stirred solution of ethyl 3-[(E,E)-3,7,11-trimethyl-2,6,10-dodecatrienylamino]-3-oxopropionate (0.115 g, 0.34 mmol) in ethanol (2 mL) at 0° C. The resulting mixture was stirred at 0° C. for 5 minutes, then warmed to room temperature and stirred for 0.5 hours. The reaction mixture was poured into brine, acidified with hydrochloric acid (5%) and extracted with ethyl acetate. The extract was washed with brine, dried, filtered and evaporated to afford the title compound (80 mg, 0.26 mmol, 76%) as a gum.

Anal for C$_{18}$H$_{29}$NO$_3$: Calcd C, 70.32; H, 9.51; N, 4.56; Found C, 70.70; H, 9.48; N, 4.80.

NMR (CDCl$_3$) δ5.20 (H, t, J=7Hz), 5.10 (2H, t, J=7Hz), 3.92 (2H, t, J=7Hz), 3.30 (2H, s), 1.9–2.15 (8H, m), 1.68 (6H, s), 1.60 (6H, s)

EXAMPLE 8

Preparation of [2-[(E,E)-3,7,11-Trimethyl-2,6,10-dodecatrienylamino]-2-oxo-ethyl]phosphonic acid monomethyl ester, potassium salt

Step 1: Dimethyl Carboxymethylphosphonate

The title compound was prepared in a similar fashion as that described in Step 2 of Example 5 except triethyl phosphonoacetate being replaced by trimethyl phosphonoacetate.

NMR (CDCl$_3$) δ3.86 (3H, s), 3.83 (3H, s), 3.07 (H, s), 3.00 (H, s).

Step 2: Dimethyl [2-[(E,E)-3,7,11-trimethyl-2,6,10-dodecatrienylamino]-2-oxo-ethyl]phosphonate The title compound was prepared in a similar manner as that described in Step 4 of Example 5 except that dimethyl carboxymethylphosphonate was used instead of diethyl carboxymethylphosphonate.

NMR (CDCl$_3$) δ6.50 (H, bs), 5.21 (H, t, J=7 Hz), 5.10 (2H, t, J=7 Hz), 3.88 (2H, t, J=7 Hz), 3.82 (3H, s), 3.78 (3H, s), 2.88 (H, s), 2.82 (H, s), 1.9–2.1 (8H, m), 1.67 (6H, s), 1.60 (6H, s).

Step 3: [2-[(E,E)-3,7,11-Trimethyl-2,6,10-dodecatrienylamino]-2-oxoethyl]phosphonic acid monomethyl ester, Potassium salt Potassium hydroxide (1N, 0.25 ml) was added to a stirred solution of dimethyl [2-[(E,E)-3,7,11-trimethyl-2,6,10-dodecatrienylamino]-2-oxo-ethyl]phosphonate in methanol (I ml) and water (0.75 ml). The resulting mixture was heated at 65°–70° C. for 1.75 hours. After cooling, the mixture was evaporated in vacuo to leave a residue. The residue was applied to a column packed with CHP20P. The column was eluted successively with water (20×12 ml) and 20% acetonitrile (20×12 ml) and the fractions were analyzed by HPLC. The fractions of high purity of the title compound were combined and lyophilized. The residue was redissolved in methanol and transferred to a small vial. The solvent was evaporated by blowing nitrogen gas to the solution, then dried under high vacuum to provide the title compound as a gum.

Anal. for C$_{18}$H$_{31}$NKO$_4$P: Calcd C, 54.66; H, 7.90; N, 3.54; Found: C, 54.71; H, 7.80; N, 3.37.

NMR (CD$_3$OD) δ5.24 (H, t, J=7 Hz), 5.10 (2H, q, J=7 Hz), 3.80 (2H, d, J=6 Hz), 3.60 and 3.57 (3H combined, 2s) 2.67 (H, s), 2.60 (H, s), 1.9~2.2 (8H, m), 1.68 (3H, s), 1.66 (3H, s), 1.60 (6H, s).

EXAMPLE 9

Preparation of [2-[(E,E)-3,7,11-trimethyl-2,6,10-dodecatrienylamino]-1-oxo-methyl]-phosphonic acid

Step 1: Dimethyl [2-[(E,E)-3,7,11-trimethyl-2,6,10-dodecatrienylamino]-1-oxo-methyl]phosphonate A mixture of (E,E)-3,7,11-trimethyl-2,6,10-dodecatrienylamine (Ca. 2.63 mmol, its preparation described in Step 3 of Example 5) and trimethyl phosphonoformate (0.44g, 2.63 mmol) in toluene (4 ml) was heated at reflux for 3 h. After cooling, the reaction mixture was concentrated in vacuo and the residue was purified by flash chromatography on a silica gel column. Elution of the column with methylene chloride, then acetone in methylene chloride (2% to 10%) to afford the title compound (96 mg, 0.27 mmol, 10%) as an oil. NMR (CDCl$_3$) δ6.90 (H, bs), 5.20 (H, t, J=7 Hz), 5.10 (2H, t, J=7 Hz), 3.94 (2H, m), 3.90 (3H, s), 3.86 (3H, s), 1.9–2.15 (8H, m), 1.67 (6H, s), 1.60 (6H, s).

Step 2: [2-[(E,E)-3,7,11-trimethyl-2,6,10-dodecatrienylamino]-1-oxo-methyl]-phosphonic acid Dimethyl [2-[(E,E)-3,7,11-trimethyl-2,6,10-dodecatrienylamino]-1-oxo-methyl]-phosphonate was deprotected in a similar fashion as that described in Step 2 of Example 2. The reaction mixture was diluted with toluene (3 ml), then evaporated to dryness. This process was repeated twice and the final residue was dissolved in methanol (2 ml) and treated with potassium hydroxide (1N, 0.57 ml). After 20 min stirring, the mixture was concentrated and the residue was applied to a column packed with CHP20P. The column was eluted successively with water (20×12 ml) and 20% acetonitrile in water, the fractions were analyzed by HPLC. The fractions of high purity of the title compound were combined and lyophilized. The residue was dissolved in methanol and transferred to a vial. The solvent was removed by evaporation followed by drying under high vacuum to afford the title compound as a gum.

NMR (CD$_3$OD) δ7.53 (H, s), 5.24 (H, t, J=7 Hz), 5.10 (2H, q, J=7 Hz), 3.86 (2H, d, J=6 Hz), 1.9~2.15 (8H, m), 1.70 (3H, s), 1.67 (3H, s), 1.60 (6H, s).

EXAMPLE 10

Preparation of [1-Hydroxy-(E,E)-3,7,11-trimethyl-2,6,10-dodecatrienyl]phosphonic acid

Step 1: Dimethyl [1-hydroxy-(E,E)-3,7,11-trimethyl-2,6,10-dodecatrienyl]phosphonate To a stirred solution of farnesal (245 mg, 1.11 mmol) in acetonitrile (1.1 ml) under argon at room temperature (r.t), was added triethylamine (0.31 ml, 2.22 mmol) and dimethyl phosphite (0.153 ml, 1.67 mmol) and the resulting mixture stirred at r.t. for 24 hr. The reaction mixture was concentrated in vacuo, the resulting residue was chromatographed over silica gel eluted with ethyl acetate to afford the title compound as a colorless oil.

NMR (CDCl$_3$) δ1.60 (6H, s), 1.68 (3H, s), 1.71 (3H, d, J=3.1 Hz), 1.80-2.30 (9H, m), 3.80 (6H, m), 4.69 (1H, dt, J=9 and 5.4 Hz), 5.00-5.20 (2H, m), 5.34 (1H, m).

Step 2: [1-Hydroxy-(E,E)-3,7,11-trimethyl-2,6,10-dodecatrienyl]phosphonic acid To a stirred solution of dimethyl [1-hydroxy -(E,E)-3,7,11-trimethyl-2,6,10-dodecatrienyl]-phosphonate (67 mg, 0.203 mmol) and 2,4,6-collidine (0.107 ml, 0.81 mmol) in dichloromethane (3 ml) under argon at 0° C., was added trimethylsilyl bromide (0.107 ml, 0.8 mmol) and the resulting mixture stirred at 0° C. for 30 min and then at r.t. for 5 hrs. The resulting white suspension was diluted with toluene (10 ml) and the solvent evaporated in vacuo, the resulting white solid was dissolved in ethylacetate and water and the pH was adjusted to pH=3 by the addition of 1M HCl solution. The organic layer was separated, dried (MgSO$_4$) and evaporated to afford a pale yellow solid. The solid was washed with dichloromethane (2×5 ml) and the white solid filtered off and dried in vacuo to afford the title compound.

NMR (DMSO-d6) δ1.55 (6H, s), 1.56 (3H, s), 1.60 (3H, d, J=2.0 Hz), 1.80-2.20 (9H, m), 4.24 (1H, dd, J=9.5 and 10.5 Hz), 5.00-5.30 (3H, m).

Anal. Calcd for C$_{15}$H$_{27}$O$_4$P.0.25 H$_2$O: C, 58.71; H, 9.03; Found: C, 58.72: H, 8.94.

EXAMPLE 11

Preparation of [1-Hydroxy-(E,E)-5,9,13-trimethyl-4,8,12-tetradecatrienyl]phosphonic acid

Step 1: (E,E)-4,8,12-Trimethyl-3,7,11-tridecatrienal

A solution of (E,E)-4,8,12-trimethyl-3,7,11-tridecatrienol (400 mg, 1.59 mmol) in acetonitrile (5 ml) was added to a slurry of N-methymorpholine N-oxide (280 mg, 2.38 mmol) and powdered 4A molecular sieves in acetonitrile (10 ml) and the mixture stirred at r.t. for 10 min. Tetrapropylammonium perruthenate (28 mg, 0.00795 mmol) was added in one portion and the resulting dark green slurry stirred at r.t for 1 hr. The reaction mixture was filtered through a plug of silica gel eluting with ethylacetate and the filtrate evaporated in vacuo. The resulting oil was chromatographed over silica gel eluting with diethylether: hexanes (1:10, v:v) to afford the title compound (200 mg, 50%) as a clear colorless oil.

NMR (CDCl$_3$) δ1.59 (6H, s) 1.63 (3H, s), 1.68 (3H, s), 1.9-2.2 (8H, m) 2.33 (2H, brq, J=7 Hz), 2.46 (2H, tt, J=1.6 and 7.0 Hz), 5.00-5.20 (3H, m), 9.76 (1H, t, J=1.6 Hz).

Step 2: Dimethyl [1-hydroxy-(E,E)-5,9,13-trimethyl-4,8,12-tetradecatrienyl]phosphonate To a stirred solution of (E,E)-4,8,12-trimethyl-3,7,11-tridecatrienal (200 mg, 0.81 mmol) in acetonitrile (0.8 ml) under argon at r.t., was added triethylamine (0.22 ml, 1.61 mmol) and dimethyl phosphite (0.11 ml, 1.21 mmol) and the resulting mixture stirred at r.t. for 4 hr. The reaction mixture was concentrated in vacuo, and the resulting residue chromatographed over silica gel eluted with ethyl acetate to afford the title compound as a colorless oil.

NMR (CDCl$_3$) δ1.60 (6H, s), 1.63 (3H, s), 1.68 (3H, s), 1.72-1.85 (2H, m) 1.90-2.40 (10H, m), 3.59 (1H, m) 3.80 (3H, d, J =11 Hz), 3.81 (3H, d, J=11 Hz) 3.89 (1H, m), 5.00-5.20 (3H, m).

Step 3: (1-Hydroxy-(E,E)-5,9,13-trimethyl-4,8,12-tetradecatrienyl]phosphonic acid To a stirred solution of dimethyl[1-hydroxy-(E,E)-5,9,13-trimethyl-4,8,12-tetradecatrienyl]-phosphonate (98 mg, 0.253 mmol) and 2,4,6-collidine (0.134 ml, 1.014 mmol) in dichloromethane (3 ml) under argon at 0° C., was added trimethylsilyl bromide (0.134 ml, 1.013 mmol) and the resulting mixture stirred at 0° C. for 30 min. and then at r.t. for 5 hr. The resulting white suspension was diluted with toluene (10 ml) and the solvent evaporated in vacuo, the resulting white solid was dissolved in ethylacetate and water and the pH was adjusted to 3 by the addition of 1M HCl solution. The organic layer was separated, dried (Na$_2$SO$_4$) and evaporated to afford a glassy residue. The solid was washed with acetonitrile (2×5 ml) and the white solid filtered off and dried in vacuo to afford the title compound.

NMR (DMSO-d6) δ1.55 (6H, s), 1.56 (3H, s), 1.62 (3H, s), 1.80-2.20 (13H, m), 3.42 (1H, m), 5.00-5.20 (2H, m).

EXAMPLE 12

Preparation of [1-Hydroxy-(E,E)-4,8,12-trimethyl-3,7,11-tridecatrienyl]phosphonic acid

Step 1: Diethyl (t-Butyldimethylsiloxy)methylphosphonate

To a stirred solution of diethyl hydroxylmethylphosphonate (2.13 g, 12.7 mmol), triethylamine (2.12 ml, 15.2 mmol) and dimethylaminopyridine (77 mg, 0.63 mmol) in dichlormethane at 0° C. under argon, at r.t., was added t-butyldimethylsilyl chloride (1.85 g, 12.8 mmol) in dichloromethane (5 ml). After 14 hr the resulting slurry was poured into water (100 ml) and extracted with dichloromethane (2×100 ml). The organic extracts were dried (Na$_2$SO$_4$), concentrated in vacuo and the resulting oil chromatographed on silica gel eluted with ethylacetate:hexanes (1:1, v:v) to afford the title compound as a clear oil.

NMR (CDCl$_3$) δ0.09 (6H, s), 0.89 (9H, s), 1.33 (6H, t, J=7.1 Hz), 3.91 (1H, d, J=8.5 Hz,), 4.14 (2H, q, J=7.1 Hz), 4.17 (2H, q, J=7.1 Hz).

Step 2: Diethyl [1-(t-Butyldimethylsiloxy)-(E,E)-4,8,12-trimethyl-3,7,11-tridecatrienyl]-phosphonate To a stirred solution of the diethyl (t-butyldimethylsiloxy)methylphosphonate (562 mg, 2.0 mmol) in THF (5 ml) under argon at −78° C. was added n-BuLi (0.84 ml of a 2.5M solution in hexanes, 2.1 mmol) and the resulting mixture stirred at −78° C. for 15 min. Farnesyl bromide (0.542 ml, 2.0 mmol) was added to the mixture over 5 min and the solution stirred a further 1 hr at −78° C. and then allowed to warm to r.t. The reaction mixture was poured into saturated NaHCO$_3$ solution and the organic solvent evaporated in vacuo, the residue was extracted into ethylacetate and washed with brine, dried (MgSO$_4$) and concentrated in vacuo and the resulting oil chromatographed on silica gel eluted with ethylacetate:hexanes (3:7, v:v). to afford the title compound as an oil.

NMR (CDCl$_3$) δ0.00 (3H, s), 0.06 (3H, s) 0.82 (9H, s), 1.25 (3H, t, J=7 Hz) 1.26 (3H, t, J=7 Hz) 1.52 (6H, s), 1.56 (3H, s), 1.61 (3H, s), 1.90–2.10 (8H, m) 2.10–2.30 (2H, m), 3.84 (1H, m), 4.00–4.10 (4H, m), 5.00–5.15 (2H, m), 5.15 (1H, brt, J=7 Hz).

Step 3: Diethyl [1-hydroxy-(E,E)-4,8,12-trimethyl-3,7,11-tridecatrienyl]phosphonate To a solution of the diethyl [1-(t-butyldimethylsiloxy)-(E,E)-4,8,12-trimethyl-3,7,11-tridecatrienyl]phosphonate (55 mg, 0.113 mmol) in THF (1 ml), under argon, at 0° C. was added tetrabutylammonium fluride (0.113 ml of a 1.0M solution in THF, 0.113 mmol), and the mixture stirred at 0° C. for 1 hr. The solvent was evaporated in vacuo and the residue chromatographed on silica gel eluted with ethylacetate:hexanes, (3:1, v:v) to afford the title compound (37 m,g 88%) as an oil.

NMR (CDCl$_3$) δ1.34 (6H, brt, J=7 Hz), 1.60 (6H, s), 1.65 (3H, s), 1.68 (3H, s), 1.90–2.20 (8H, m), 2.30–2.60 (2H, m), 2.8 (1H, br s), 3.86 (1H, dt J=8.9 and 4.6 Hz) 4.17 (2H, q, J=7.1Hz), 4.19 (2H, q, J=7.1 Hz), 5.00–5.15 (2H, m), 5.25 (1H, brt, J=7 Hz)

Step 4: [1-Hydroxy-(E,E)-4,8,12-trimethyl-3,7,11-tridecatrienyl]phosphonic acid

To a stirred solution of diethyl [1-hydroxy-(E,E)-4,8,12-trimethyl-3,7,11-tridecatrienyl]-phosphonate (37 mg, 0.0993 mmol) and 2,4,6-collidine (0.052 ml, 0.397 mmol) in dichloromethane (3 ml) under argon at 0° C., was added trimethylsilyl bromide (0.052 ml, 0.397 mmol) and the resulting mixture stirred at 0° C. for 30 min and then at r.t. for 4 hr. The resulting white suspension was diluted with toluene (10 ml) and the solvent evaporated in vacuo. The resulting white solid was dissolved in ethylacetate and water and the pH was adjusted to 3 by the addition of 1M HCl solution. The organic layer was separated and dried (MgSO$_4$) and evaporated to afford a clear oil. Addition of acetonitrile 2 ml precipitated the title compound as an off white solid which was removed by filtration and dried in vacuo.

NMR (DMSO-d6) δ1.55 (9H, s), 1.62 (3H, s), 1.80–2.40 (11H, m), 3.40 (1H, m), 5.00–5.15 (2H, m), 5.25 (1H, m). Mass:m/e 315 (M-H$^+$)

EXAMPLE 13

Preparation of [2-Acetamido-(E,E)-4,8,12-trimethyl-3,7,11-tridecatrienyl]phosphonic acid Step 1: Dimethyl [2-hydroxy-(E,E)-4,8,12-trimethyl-3,7,11-tridecatrienyl]phosphonate n-Butyllithium (0.698 ml of a 2.5M solution in hexanes, 1.75 mmol) was added to a stirred solution of dimethyl methylphosphonate (0.189 ml, 1.75 mmol) in THF (4 ml), under argon at −78° C. The resulting colorless solution was stirred at this temperature for 20 min. Farnesal (350 mg, 1.59 mmol) in THF (4 ml) was added over 5 min and the resulting mixture stirred a further 30 min and then treated with saturated sodium bicarbonate solution (5 ml) and allowed to warm to r.t. The THF was evaporated in vacuo and the aqueous extracted twice with ethylacetate, washed with brine, dried (MgSO$_4$) and concentrated in vacuo. The residue was chromatographed on silica gel eluted with ethylacetate to afford the title compound as an oil.

NMR (CDCl$_3$) δ1.59 (6H, s), 1.68 (3H,s), 1.70 (3H, s), 1.80–2.20 (1H, m) 3.0 (1H, d, J=2.7 Hz), 3.76 (3H, d, J=11 Hz) 3.77 (3H, d, J=10.8 Hz) 4.80 (1H, m), 5.10 (2H, m), 5.25 (1H, brd, J=9.5 Hz).

Step 2: Dimethyl (2-amino-(E,E)-4,8,12-trimethyl-3,7,11-tridecatrienyl]-phosphonate To a stirred solution of the dimethyl [2-hydroxy-(E,E)-4,8,12-trimethyl-3,7,11-trideatrienyl]-phosphonate (174 mg, 0.505 mmol), triphenylphosphine (197 mg, 0.758 mmol) and phthalidide (89 mg, 0.606 mmol) under argon at r.t. in THF (1.6 ml) was added diethylazodicarboxylate (0.119 ml, 0.759 mmol) over 2 min. After 2 hrs the reaction mixture was concentrated in vacuo and chromatographed on silica gel gradient eluted with ethyl acetate:hexanes (1:1, v:v) to (3:2, v:v) to afford the phthalimide derivative (181 mg, 0.382 mmol) contaminated with triphenylphospine oxide which was not further purified. The phthalimide derivative (181 mg, 0.382 mmol), hydrazine (0.12 ml, 3.82 mmol) in methanol (3.8 ml) was stirred under argon at r.t. for 20 min and then heated at reflux for 24 hr. Upon cooling a white precipitate was obtained and removed by filtration. The filtrate was concentrated in vacuo and chromatographed on silica gel eluted with methylene chloride:methanol:ammomiun hydroxide (95:5:0.2, v:v:v) to afford the title compound as an oil.

NMR (CDCl$_3$) δ1.61 (6H, s), 1.68 (6H, s), 1.80–2.20 (12H, m), 3.76 (6H, d, J=10 Hz) 4.07 (1H, m), 5.00–5.20 (3H, m).

Step 3: Dimethyl[2-acetamido-(E,E)-4,8,12-trimethyl-3,7,11-trideatrienyl]phosphate To a solution of dimethyl [2-amino-(E,E)-4,8,12-trimethyl-3,7,11-tridecatrienyl]phosphonate (50 mg, 0.145 mmol) dimethylaminopyridine (9 mg, 0.073 mmol) and triethylamine (0.061 ml, 0.435 mmol) at r.t. under argon was added acetic anhydride (0.041 ml, 0.435 mmol). After 30 min. the reaction was concentrated in vacuo and chromatographed on silica gel eluting with methanol:dichloromethane, 97, v:v to afford the title product as an oil.

NMR(DMSO-d6) δ1.55 (6H, s), 1.64 (6H, s), 1.75 (3H, s) 1.80–220 (10H, m), 3.55 (3H, s), 3.6 (3H, s) 4.73 (1H, m) 5.00–5.15 (2H, m), 888 (1H, d, J=8 Hz).

Step 4:

[2-Acetamido-(E,E)-4,8,12-trimethyl-3,7,11-tridecatrienyl]phosphonic acid

To a stirred solution of dimethyl 2-acetamido-(E,E)-4,8,12-trimethyl-3,7,11-tridecatrienyl]phosphonate (39 mg, 0.101 mmol) and 2,4,6-collidine (0.054 ml, 0.404 mmol) in dichloromethane (2.5 ml) under argon at 0° C., was added trimethylsilyl bromide (0.054 ml, 0.404 mmol) and the resulting mixture stirred at 0° C. for 30 min and then at r.t. for 5 hr. The resulting white suspension was diluted with toluene (10 ml) and the solvent evaporated in vacuo. The resulting white solide was dissolved in ethylacetate and water and the pH was adjusted to 3 by the addition of 1M HCl solution. The organic layer was separated, dried ($Na_2SO_4$) and evaporated to afford a clear oil, which was dissolved in hexanes and treated with 10 drops of ammonium hydroxide, the precipitate was removed by filtration and dried in vacuo to afford the title compound as an off white solid.

NMR (DMSO-d6) δ1.54 (6H, s), 1.61 (3H, s), 1.62 (3H, s), 1.73 (3H, S), 1.80–2.10 (10H, M), 4.72 (1H, m), 5.00–5.15 (2H, m), 6.92 (1H, s), 7.10 (1H, s) 7.27 (1H, s), 7.78 (1H, d, J=8 Hz)

Anal Calcd for $C_{18}H_{35}NO_4p$ 1.01 $H_2O$, 0.92 $NH_3$: C, 55.25; H, 9.47; N, 6.90; Found: C, 55.23; H, 9.47; N, 6.90.

EXAMPLE 14

Preparation of [2-Hydroxy-(E,E)-4,8,12-trimethyl-3,7,11-tridecatrienyl]phosphonic acid, Ammonium salt Dimethyl [2-hydroxy-(E,E)-4,8,12-trimethyl-3,7,11-tridecatrienyl]-phosphonate was deprotected in a similar fashion as described in Step 2 of Example 2 to afford [2-hydroxy-(E,E)-4-8,12-trimethyl-3,7,11-tridecatrienyl]phosphonic acid. This acid was dissolved in methanol, treated with ammonium hydroxide and the title compound precipitated out as a white solid.

NMR (DMSO-d6) δ7.32 (H, s), 7.16 (H, s), 6.98 (H, s), 4.95–5.2 (3H, m), 4.51 (H, m), 1.8–2.2 (11H, m), 1.62 (3H, s), 1.60 (3H, s), 1.55 (6H, s).

Anal Calcd for $C_{16}H_{29}O_4P \cdot 1.73\ NH_3 \cdot 0.43\ H_2O$: C, 54.34; H, 9.99; N, 6.86; Found: C, 54.33; H, 9.75; N, 6.88.

What is claimed is:

1. A compound of the formula:

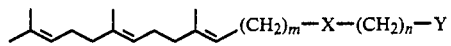

wherein:
X is CH(OH);
Y is COOH
m is 0, 1, 2 or 3; and
n is 0, 1, 2 or 3.
or the pharmaceutically acceptable salts thereof.

2. The compound according to claim 1 which is

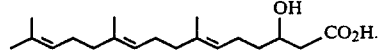

3. A pharmaceutical composition comprising a pharmaceutical carrier and, dispersed therein, a therapeutically effective amount of the compound of claim 1.

* * * * *